(12) United States Patent
Smith

(10) Patent No.: US 7,247,492 B2
(45) Date of Patent: Jul. 24, 2007

(54) METHOD FOR OBSERVING CHEMICAL SUBSTANCES

(75) Inventor: George E. Smith, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 380 days.

(21) Appl. No.: 10/222,315

(22) Filed: Aug. 15, 2002

(65) Prior Publication Data
US 2003/0000954 A1 Jan. 2, 2003

Related U.S. Application Data

(62) Division of application No. 09/644,371, filed on Aug. 23, 2000, now Pat. No. 7,059,491.

(51) Int. Cl.
*G01N 31/16* (2006.01)
(52) U.S. Cl. ............... 436/163; 436/164; 436/165; 436/166; 436/169
(58) Field of Classification Search .......... 422/56, 422/58, 61, 99–104; 436/164, 166, 169, 436/163, 165; 356/246
See application file for complete search history.

(56) References Cited

U.S. PATENT DOCUMENTS

| 514,426 A | 2/1894 | Outerbridge, Jr. |
| 2,549,574 A * | 4/1951 | Condiff .................. 356/246 |
| 2,984,035 A | 5/1961 | Nalle, Jr. |
| 2,989,813 A | 6/1961 | Hess, Sr. |
| 3,045,495 A | 7/1962 | Spencer et al. |
| 3,286,583 A | 11/1966 | Ferrari |
| 3,338,458 A | 8/1967 | Hultgren |
| 3,381,572 A | 5/1968 | Tuwiner |
| 3,514,887 A | 6/1970 | Jacob |
| 3,515,262 A | 6/1970 | Ornstein et al. |
| 3,766,116 A | 10/1973 | Olhoft |
| 3,874,977 A | 4/1975 | Pyles |
| 3,880,012 A | 4/1975 | Shapcott |
| 3,912,100 A | 10/1975 | Graham et al. |
| 4,071,597 A | 1/1978 | Karabedian |
| 4,237,234 A * | 12/1980 | Meunier .................. 435/287.7 |

(Continued)

OTHER PUBLICATIONS

"Titrimetric Analysis-Standardization of a 0.1 Molar NaOH Titrant", www.chem.queensu.ca, pp. 1-4, no date.*

*Primary Examiner*—Lyle A. Alexander
(74) *Attorney, Agent, or Firm*—Perkins Coie LLP

(57) ABSTRACT

An apparatus and method for observing a chemical substance. In one embodiment, the apparatus includes a vessel having a base portion and an at least partially transparent wall portion depending from and extending away from the base portion. The base portion and the wall portion define an interface region at an interface between the base portion and the wall portion. The vessel can further include a background material fixedly attached to the base portion and/or the interface region, with the background material having a surface visible through the wall portion from a region exterior to the vessel. The background material can be attached to an inner surface or an outer surface of the vessel, or the background material can be integrated with a medium that forms the base portion and the wall portion of the vessel. The background material can have a single color, such as white or black, or the background material can have a plurality of hues to make the contents of the vessel more clearly visible.

18 Claims, 3 Drawing Sheets

U.S. PATENT DOCUMENTS

| | | |
|---|---|---|
| 4,263,734 A | 4/1981 | Bradshaw |
| 4,315,573 A | 2/1982 | Bradley et al. |
| 4,443,289 A | 4/1984 | Kö lges et al. |
| 4,789,073 A | 12/1988 | Fine |
| 4,910,054 A | 3/1990 | Collette et al. |
| 5,464,107 A | 11/1995 | Koeniger |
| 5,553,735 A | 9/1996 | Kimura |
| 5,758,440 A | 6/1998 | Yudin |
| 5,953,170 A | 9/1999 | Glancy |
| 6,015,002 A | 1/2000 | Biro et al. |
| 6,378,906 B1 | 4/2002 | Pennaz |
| 6,379,620 B1 * | 4/2002 | Tydings et al. ............... 422/58 |

* cited by examiner

METHOD FOR OBSERVING CHEMICAL
SUBSTANCES

CROSS REFERENCE TO RELATED
APPLICATION

This application is a divisional of U.S. patent application Ser. No. 09/644,371, filed on Aug. 23, 2000 now U.S. Pat. No. 7,059,491.

TECHNICAL FIELD

The present invention is directed to methods and apparatuses for observing chemical substances and processes, such as liquid chemical titrations.

BACKGROUND OF THE INVENTION

Many chemistry practitioners rely on visual observations to determine when chemical processes and reactions are complete. For example, one conventional technique for determining the concentration of an acid is to titrate the acid by adding a basic solution of a known concentration to the acid until the endpoint is achieved. When the acid/base solution reaches the end point (i.e., the point at which the exact amount of necessary base has been added to completely react with the acid), the color of a chemical indicator in the acid/base solution changes. The practitioner can then calculate the concentration of the acid by measuring the quantity of the base that was required to reach the end point.

One characteristic feature of the technique described above is that the chemical indicator may change color very rapidly. Accordingly, the practitioner must pay close attention to the process to determine exactly when the color change begins. Another characteristic feature is that the color change may initially be subtle, again requiring close attention on the part of the practitioner. Accordingly, a drawback with this technique is that it can be difficult to accurately and consistently determine the end point of the target chemical, particularly if the practitioner fails to observe the initial color change.

One approach to addressing the foregoing drawback is to conduct the titration process in a flat-bottomed vessel such as an Erlenmeyer flask, and place the bottom of the flask against a white background, such as a sheet of paper or paper towel. By viewing the chemical solution against a white background, the practitioner can more readily determine when the solution changes color. However, this approach can have several additional drawbacks. For example, if the practitioner uses a slightly differently colored background material for successive titrations, the practitioner may not achieve consistent or repeatable titration results. Furthermore, the practitioner may wish to move the flask to achieve an optimal viewing angle, which can be awkward if the practitioner must also move a piece of paper or paper towel held against a surface of the flask. Still further, the practitioner's view of the chemical solution in the flask may be distorted by the curvature of the flask at the juncture between the bottom of the flask and the walls of the flask, particularly when the volume of the chemical in the flask is relatively small.

SUMMARY

The present invention is directed toward apparatuses and methods for observing chemical substances. A vessel in accordance with one aspect of the invention includes a base portion and an optically transmissive wall portion projecting away from the base portion at an interface region. The base portion and the wall portion define an exterior region and an interior region, with the interior region being configured to contain a chemical substance and having an opening configured to removably receive the chemical substance. The vessel further includes a background material having a first surface and a second surface facing opposite from the first surface. The first surface of the background material is fixedly attached to the base portion and/or the interface region and is visible through the wall portion of the vessel from the exterior region of the vessel.

In a further aspect of the invention, the background material can include a paint layer disposed adjacent to the interior or the exterior surface of the vessel. Alternatively, the background material can be integrated with the vessel between an inner surface and an outer surface of the vessel. The background material can have a single hue, such as white or black, or alternatively, the background material can have a plurality of hues.

The invention is also directed toward a method for visually monitoring a chemical substance. In one aspect of the invention, the method can include disposing a chemical substance in a vessel that includes a base portion and a wall portion extending away from the base portion at an interface region. The method can further include positioning the chemical substance at least proximate to a background material fixedly attached to the vessel and covering at least a part of the base portion and/or at least part of the interface region. The method can still further include moving the vessel and the background material as a unit and viewing the chemical substance and the background material simultaneously through a transparent region of the wall portion.

The invention is also directed toward a method for forming a vessel for observing a chemical substance. In one aspect of the invention, the method can include forming a base portion of the vessel and forming an at least partially transparent wall portion depending from and extending away from the base portion at an interface region. The base portion and the wall portion define an exterior region and an interior region, with the interior region being configured to contain the chemical substance and having an opening configured to removably receive the chemical substance. The method can still further include fixedly applying a background material to the base portion and/or the interface region, with the background material having a surface visible through the wall portion from the exterior region of the vessel.

DETAILED DESCRIPTION

The present disclosure describes vessels for supporting chemical substances and methods for making and using such vessels. Many specific details of certain embodiments of the invention are set forth in the following description and in FIGS. 1-5 to provide a thorough understanding of these embodiments. One skilled in the art, however, will understand that the present invention may have several additional embodiments, or that the invention may be practiced without several of the details described below.

Figure 1:
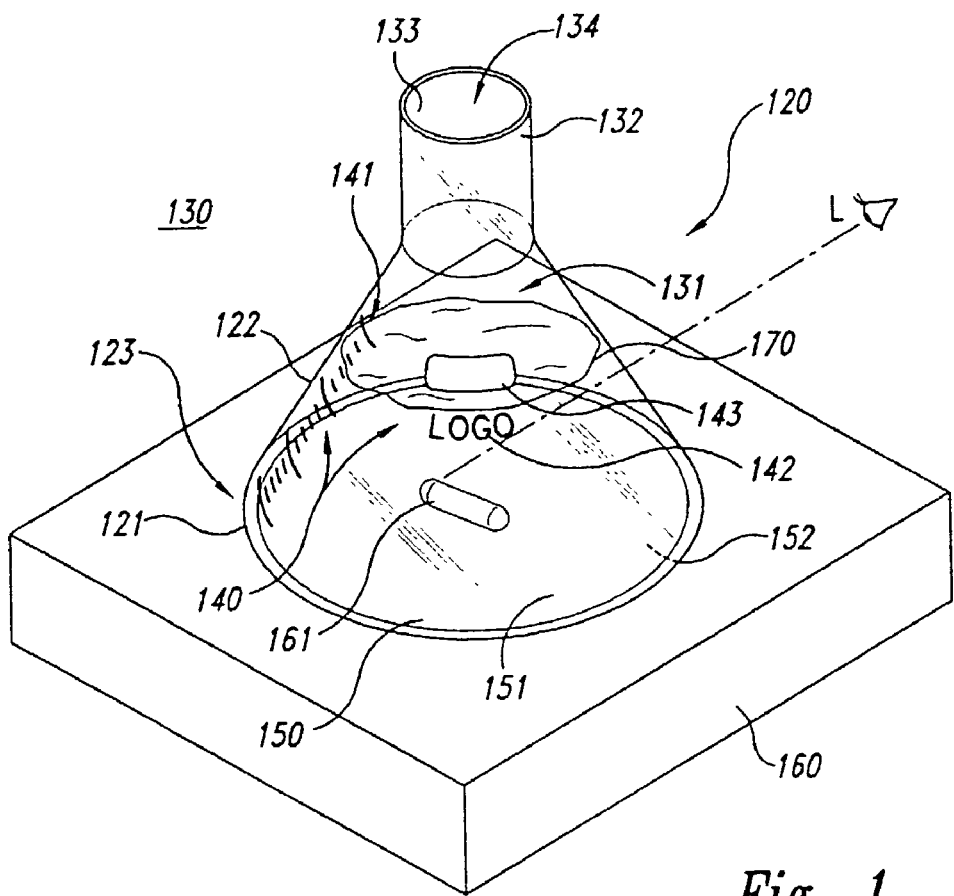
FIG. 1 is an isometric view of a vessel having an attached background material in accordance with an embodiment of the invention.

FIG. 1 is a top isometric view of a vessel 120 having a fixedly attached background material 150 in accordance with an embodiment of the invention. In one aspect of this embodiment, the vessel 120 includes a generally flat base portion 121 connected to an upwardly extending wall portion 122 at an interface region 123. In a further aspect of this embodiment, the base portion 121, the wall portion 122 and the interface region 123 can be integrally formed with each other. Alternatively, the base portion 121 can initially be separate from the wall portion 122 and can subsequently be joined at the interface region 123. In either embodiment, the base portion 121, the wall portion 122, and the interface region 123 each have an external surface 132 that defines an exterior region 130 outside the vessel 120 and an internal surface 133 that defines an interior region 131 inside the vessel 120. The interior region 131 includes an opening 134 that allows a liquid, gel, solid or gaseous chemical substance 170 to be placed within the vessel 120.

In one embodiment, the medium (such as glass or plastic) forming the base portion 121, the wall portion 122, and the interface region 123 is generally transparent or otherwise optically transmissive. Accordingly, a practitioner can view the chemical substance 170 from the exterior region 130 of the vessel 120. In one aspect of this embodiment, the background material 150 is fixedly attached to the external surface 132 of the base portion 121. For example, the background material 150 can form a layer having an interior-facing surface 151 facing toward the interior region 131 of the vessel 120, and an exterior-facing surface 152 facing toward the external region 130. Because both the wall portion 122 and the base portion 121 are transparent, the practitioner can view the chemical substance 170 against the background material 150 through the wall portion 122 and the base portion 121, as indicated by line of sight "L."

The background material 150 can have several configurations, and in each configuration, the background material 150 can be fixedly attached to the vessel 120. For example, in one embodiment, the background material 150 can include a sheet of paper, plastic, or other material that is adhesively attached to the vessel 120. Alternatively, the background material 150 can include a pigment (such as a paint) that is directly applied to the external surface 132 of the vessel 120. For example, the pigment can be sprayed or brushed onto the external surface 132. In either of these embodiments, the background material 150 can cover part or all of the base portion 121. Alternatively, the background material 150 can cover other parts of the vessel 120 in addition to or in lieu of the base portion 121, as will be described in greater detail below with reference to FIGS. 2-5.

In still a further aspect of an embodiment of the vessel 120 shown in FIG. 1, the background material 150 can have a single color or hue, such as white, black or any other suitable color. The color of the background material 150 can be selected to make the chemical substance 170 or selected constituents of the chemical substance 170 more clearly visible. In other embodiments, the background material 150 can have more than one color, as will be described in greater detail below with reference to FIG. 5. In any of these embodiments, the background material 150 can be generally opaque or, alternatively, the background material 150 can be translucent.

In one embodiment, the vessel 120 can have an Erlenmeyer flask configuration. Accordingly, the base portion 121 can be generally circular and the wall portion 122 can include an frustro-conical section adjacent to the base portion 121, and a cylindrical section above the frustro-conical. In other embodiments, the vessel 120 can have other shapes, for example, a generally cylindrical shape as will be described below with reference to FIG. 4. The vessel 120 can also include markings 140, such a graduation markings 141, a content label 143, and/or a manufacturer's logo 142. In other embodiments, the vessel 120 can include more or fewer markings 140.

In a method in accordance with one embodiment of the invention, the practitioner can use the vessel 120 to titrate the chemical substance 170. Accordingly, the practitioner can place a magnetic stirrer 161 in the vessel 120, and can place the vessel on an electric stir plate 160. As the stirrer 161 circulates the contents of the vessel 120, the practitioner can add a titrating agent to the interior region 131 of the vessel through the opening 134 while viewing the chemical substance 170 against the background material 150. Once the practitioner notes a change in color of the chemical substance 170 (or a change in color of an indicator dye added to the chemical substance 170), the practitioner halts the flow of titrating agent into the vessel 120 and measures the total amount of titrating agent added to the vessel.

Alternatively, the vessel 120 can be used in accordance with other embodiments of the invention. For example, the practitioner can observe the contents of the vessel 120 without placing the vessel on the stir plate 160. In another embodiment, the practitioner can observe the formation of a precipitate within the vessel 120, in addition to or in lieu of observing a color change of the contents of the vessel 120, as will be described in greater detail below with reference to FIG. 4. In still further embodiments, the practitioner can use the vessel 120 in other ways, for example, to observe other types of chemicals and/or chemical reactions, so long as the practitioner is able to view the contents of the vessel 120 against the background material 150.

One feature of an embodiment of the vessel 120 described above with reference to FIG. 1 is that the background material 150 is fixedly attached to the vessel 120. An advantage of this feature is that the practitioner can move the vessel 120 without having to separately support and move an adjacent piece of background material, such a sheet of paper or paper towel. Accordingly, an embodiment of the vessel 120 is simpler and easier to use than some conventional arrangements in which the practitioner must keep the vessel aligned with a suitable background while observing the contents of the vessel.

Another advantage of this feature is that the color of the background material 150 can remain consistent from one vessel 120 to another because the vessel manufacturer can control the constituent(s) used for the background material. Accordingly, practitioners can obtain more reliable and consistent results when using several different vessels 120. Still another advantage is that the interior-facing surface 151 of the background material 150 can be positioned tightly against the external surface 132 of the vessel 120 in one embodiment. Accordingly, the interior-facing surface 151 can be protected from environmental hazards, such as moisture and other contaminants that can discolor the interior-facing surface 151. As a result, the background material 150 can retain its initial color for longer than can some conventional detached background materials.

Figure 2:
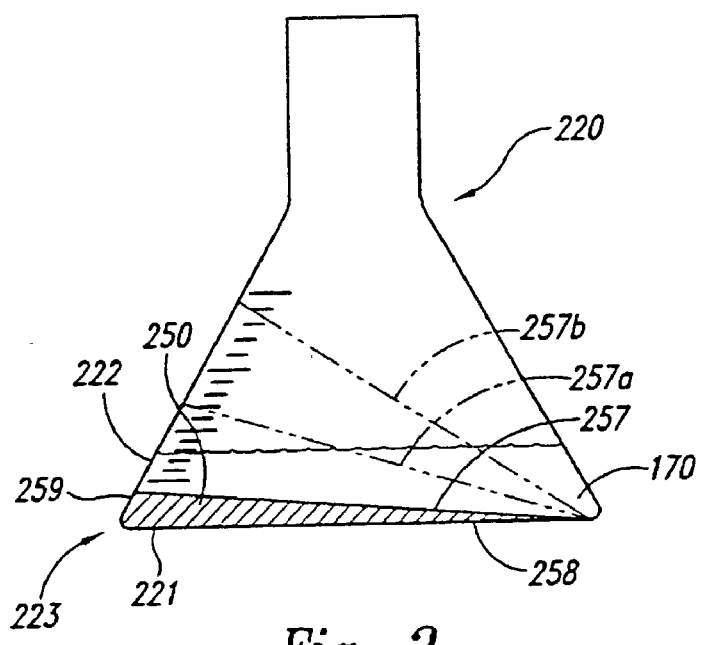
FIG. 2 is a side elevation view of a vessel having an attached background material that extends upwardly from a base portion of the vessel in accordance with another embodiment of the invention.

FIG. 2 is a side elevational view of a vessel 220 having a background material 250 configured in accordance with another embodiment of the invention. In one aspect of this embodiment, the vessel 220 has a base portion 221, a wall portion 222, and an interface region 223 between the base portion 221 and the wall portion 222. The background material 250 can include a lower part 258 adjacent to the base portion 221 and an upper part 259 adjacent to the interface region 223. In a further aspect of this embodiment, the background material 250 can initially be in a liquid form and can be applied to the vessel 220 by canting the vessel 220 at an angle and partially immersing the vessel 220 in a volume of the liquid background material 250. Accordingly, the background material 250 can have an elliptical periphery 257 that extends around the vessel 220 from the base portion 221 into the interface region 223. Alternatively, the background material 250 can extend upwardly beyond the interface region 223 to cover part of the wall portion 222, and can accordingly have a more highly canted, elliptical periphery 257a or 257b. In other embodiments, the background material 250 can have other shapes and configurations, so long as the background material 250 covers at least part of the base portion 221 and/or at least part of the interface region 223 of the vessel 220.

One feature of an embodiment of the vessel 220 described above with reference to FIG. 2 is that the background material 250 covers at least part of the base portion 221 and the interface region 223. An advantage of this feature is that the practitioner can view the chemical substance 170 within the vessel 220 against both the lower part 258 and the upper part 259 of the background material 250. Accordingly, the practitioner can be more likely to detect a change in the appearance of the chemical substance 170 immediately after the change occurs. Another feature of an embodiment of the vessel 220 described above with reference to FIG. 2 is that the periphery 257 of the background material 250 has an elliptical shape. Accordingly, the background material 250 can cover part of the interface region 223 and/or the wall portion 222, while the remainder of the wall portion 222 is uncovered to give the practitioner a clear view of the chemical substance 170.

Figure 3A:
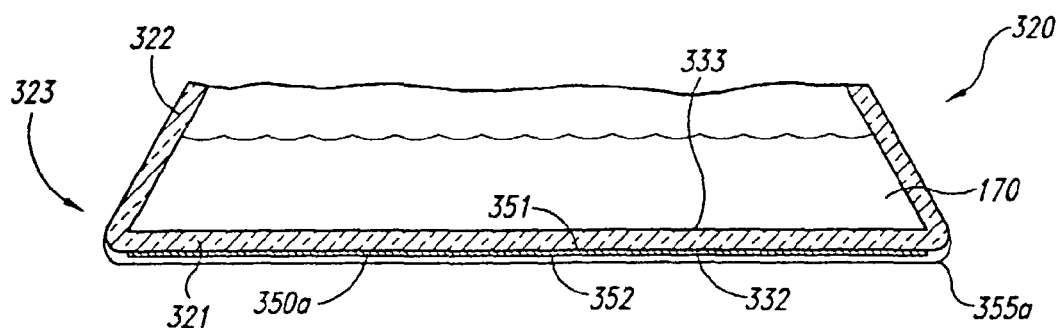
FIGS. 3A-3C are cross-sectional, side elevation views of a portion of a vessel having background materials attached in accordance with several embodiments of the invention.
Figure 3B:
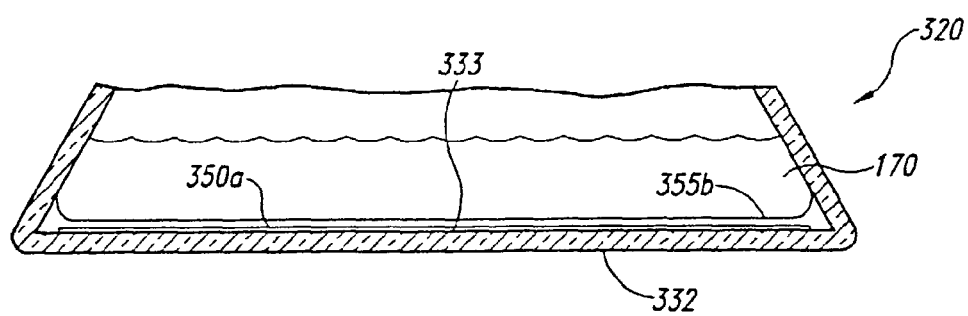
Figure 3C:
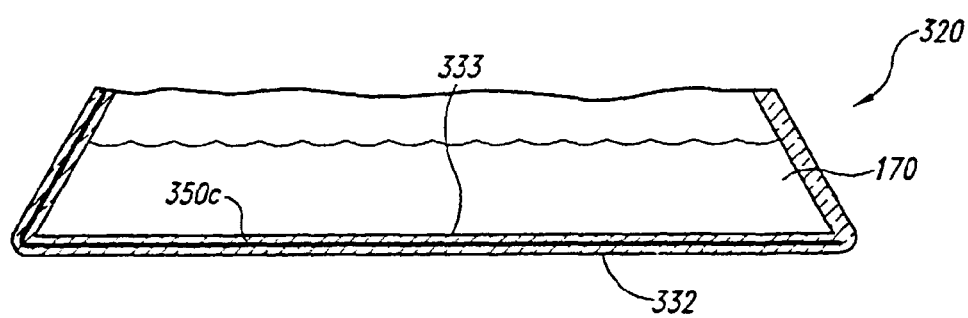

FIGS. 3A-3C are cross-sectional side elevational views of a portion of a vessel 320 having background materials applied in accordance with further embodiments of the invention. Referring first to FIG. 3A, the vessel 320 can include a base portion 321 attached at an interface region 323 to a wall portion 322. The wall portion 322, the interface region 323, and the base portion 321 can each have an internal surface 333 and an external surface 332. A background material 350a is applied to the external surface 333, for example, by adhesively attaching a sheet of the background material 350a to the external surface 332 or by coating the external surface 332 with a liquid background material 350a. In a further aspect of this embodiment, a protective coating 355a is applied to the background material 350a after it is attached to the external surface 332. An advantage of this feature is that that protective coating 355a can reduce the likelihood that the background material 350a will separate from the vessel 320. Another advantage is that the protective coating 355a can reduce the likelihood for discoloring the background material 350a, for example by preventing contaminants from soaking through the background material 350a from an exterior-facing surface 352 of the background material 350a to an interior-facing surface 351.

In another aspect of this embodiment, the internal surface 333 and/or the external surface 332 of the vessel 320 can be treated to protect the background material 350a. For example, the internal surface 333 and/or the external surface 332 can include an ultraviolet coating that can reduce discoloration of the background material 350a. Alternatively, the ultraviolet coating can be positioned between the internal surface 333 and the external surface 332 to protect the coating from exposure to the chemical substance 170 and/or contaminants external to the vessel 320.

Referring now to FIG. 3B, the vessel 320 can alternatively include a layer of background material 350b applied to the internal surface 333 of the vessel 320 in accordance with another embodiment of the invention. Accordingly, the background material 350b can include a paint, pigment, and/or other material coating selected to be compatible with the chemical substance 170 within the vessel 320. In a further aspect of this embodiment, a protective coating 355b (also selected to be compatible with the chemical substance 170) can be applied over the background material 350b to further isolate the background material 350b from the chemical substance 170 within the vessel 320.

FIG. 3C is a cross-sectional side elevational view of a portion of the vessel 320 having a background material 350c integrated with the medium forming the base portion 321, the interface region 323, and the wall portion 322 of the vessel 320. For example, when the medium includes glass, the background material 350c can be disposed in the glass between the internal surface 333 and the external surface 332 using known techniques. An advantage of integrating the background material 350c with the medium forming the vessel 320 is that the background material 350c can be isolated from both the chemical substance 170 within the vessel 320 and environmental contaminants external to the vessel 320 without the need for a protective coating.

Figure 4:
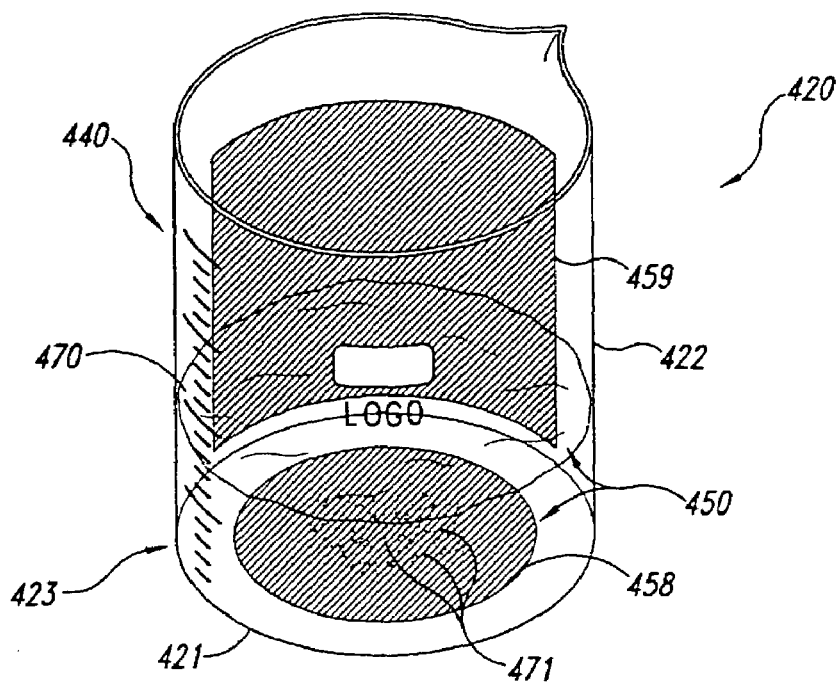
FIG. 4 is an isometric view of a vessel and attached background material configured in accordance with another embodiment of the invention.

FIG. 4 is an isometric view of a vessel 420 having a background material 450 configured in accordance with another embodiment of the invention. In one aspect of this embodiment, the vessel 420 can include a generally circular base portion 421 coupled to a generally cylindrical wall portion 422 at an interface region 423. The background material 450 can include a lower part 458 that covers part or all of the base portion 421, and an upper part 459 that covers part of the wall portion 422. The lower part 458 and/or the upper part 459 can optionally extend into the interface region 423. The vessel 420 can also include markings 440 generally similar to those described above with reference to FIG. 1.

In one aspect of an embodiment of the vessel 420 described above with reference to FIG. 4, the background material 450 can have a dark color or hue, such as black. Accordingly, the vessel 420 can be particularly suited for observing light-colored materials, such as a precipitate 471 that can settle out from a liquid chemical substance 470 within the vessel 420. In other embodiments, the background material 450 can have other colors or hues selected on the basis of the color of the chemical substance 470 and/or the process that the chemical substance 470 undergoes in the vessel 420. Accordingly, the practitioner can select a vessel 420 having a background material 450 that highlights the end point or other relevant indicator point of the process taking place in the vessel 420.

Figure 5:
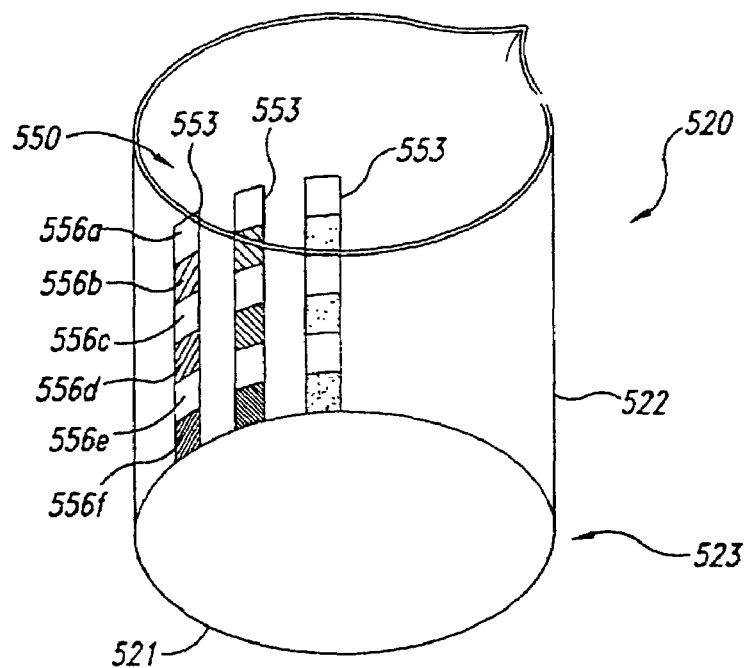
FIG. 5 is an isometric view of a vessel having multi-colored background materials attached in accordance with still another embodiment of the invention.

FIG. 5 is a side isometric view of a vessel 520 having a background material 550 with multiple hues in accordance with another embodiment of the invention. In one aspect of this embodiment, the background material 550 can be configured to form a plurality of strips 553, each having a plurality of colors. For example, in one aspect of this embodiment, the background material 550 can form three strips 553 and each strip 553 can have six colors, identified in FIG. 5 as colored portions 556a-556f. In a further aspect of this embodiment, each of the three strips 553 can have identical colors. Alternatively, each strip 553 can have different colors. In either embodiment, the strips 553 can be positioned adjacent to a wall portion 522 and an interface region 523 of the vessel 520 (as shown in FIG. 5) or, the strips 553 can be positioned adjacent to a base portion 521 of the vessel 520. In other embodiments, the background material 550 can have other shapes and/or other configurations.

One feature of an embodiment of the vessel 520 described above with reference to FIG. 5 is that the background material 550 can have a plurality of colors. An advantage of this feature is that the vessel 520 may be particularly suitable for observing chemical reactions for which the outcome can have one or more of a variety of colors. For example, some conventional methods for determining the pH of the chemical substance 470 can produce a different color depending upon the pH of the chemical substance. By having representative colors fixedly attached to the vessel 520, the practitioner can readily determine the pH of the chemical substance 470 by matching the color of the chemical substance to the appropriate colored portion 556a-556f. Another advantage is that the vessel 520 can be used for different chemical reactions (not necessarily pH tests) for which the expected outcome of the chemical reaction can have a variety of different colors. Accordingly, the practitioner can use a single vessel 520 for a variety of chemical reactions.

From the foregoing it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method for visually monitoring a chemical substance, comprising:
    disposing the chemical substance in a vessel that includes a base portion, a wall portion extending away from the base portion and having at least one transparent region, and an interface region at an interface between the wall portion and the base portion, the base portion, the wall portion and the interface region defining an inner surface and an outer surface opposite the inner surface, wherein the chemical substance is disposed adjacent to the inner surface;
    positioning the chemical substance at least proximate to a background material incorporated into the vessel with the background material covering at least part of the base portion and at least part of the interface region, wherein the background material is positioned between the inner surface and the outer surface, between the outer surface and a protective coating, or between the inner surface and the chemical substance;
    disposing a chemical indicator in the vessel;
    disposing a titrating substance in the vessel;
    stirring the contents of the vessel; and
    detecting an equivalence point of the contents of the vessel by comparing an appearance of the chemical substance through the inner and/or outer surface of the vessel wall while the chemical substance is positioned adjacent to the background material and determining an amount of the titrating substance added to the vessel when the contents of the vessel changes from a first color to a second color.

2. The method of claim 1 wherein detecting an equivalence point includes viewing the background material through the inner and outer surfaces.

3. The method of claim 1 wherein detecting an equivalence point includes viewing the background material through the inner surface of the medium and through a part of the medium between the inner surface and the background material.

4. The method of claim 1, further comprising grasping the vessel without separately grasping the background material.

5. The method of claim 1 wherein detecting an equivalence point includes viewing a first hue of the background material and a second hue of the background material different than the first hue.

6. The method of claim 1 wherein detecting an equivalence point includes viewing a white portion of the background material.

7. The method of claim 1 wherein detecting an equivalence point includes viewing a black portion of the background material.

8. The method of claim 1 wherein the background material covers at least approximately the entire base portion, and wherein the method includes viewing the chemical substance against the base portion.

9. The method of claim 1 wherein the background material extends over at least a first part of the base portion and a second part of the wall portion, and wherein the method further comprises viewing the chemical substance against both the first and second parts.

10. The method of claim 1 wherein disposing the chemical substance includes disposing a liquid chemical substance.

11. The method of claim 1 wherein detecting an equivalence point includes viewing a liquid portion of the chemical substance and viewing a solid precipitate of the chemical substance.

12. A method for visually monitoring a chemical substance, comprising:
    disposing the chemical substance in a vessel having a base portion, a wall portion extending away from the base portion and having at least one transparent region, and an interface region at an interface between the wall portion and the base portion, the base portion, the wall portion and the interface region defining an inner surface and an outer surface opposite the inner surface, wherein the chemical substance is disposed adjacent to the inner surface;
    positioning the chemical substance at least proximate to a background material incorporated into the vessel with the background material covering at least part of the base portion and at least part of the interface region, the background material having a first region with a first hue and a second region with a second hue different than the first hue, wherein the background material is positioned between the inner surface and the outer surface, between the outer surface and a protective coating, or between the inner surface and the chemical substance;
    disposing a chemical indicator in the vessel;
    disposing a titrating substance in the vessel; and
    detecting an equivalence point of the contents of the vessel by comparing an appearance of the chemical substance through the inner and/or outer surface of the vessel wall while the chemical substance is positioned adjacent to the background material and determining an amount of the titrating substance added to the vessel when the contents of the vessel changes from a first color to a second color.

13. The method of claim 12 wherein detecting an equivalence point includes viewing the background material through the inner and outer surfaces of the medium.

14. The method of claim 12 wherein detecting an equivalence point includes viewing the background material through the inner surface and through a part of the medium between the background material and the inner surface.

15. The method of claim 12, further comprising comparing a color of the chemical substance to at least one of the first hue and the second hue.

16. The method of claim 12 wherein the background material includes a first part extending over at least part of the wall portion and a second part extending over at least part of the base portion, and wherein the method further comprises viewing the chemical substance against both the first and second parts of the background material.

17. A method for titrating a liquid chemical substance, comprising:

disposing the liquid chemical substance and an indicator in a vessel having a base portion and a generally transparent wall portion extending away from the base portion, the base portion and the wall portion defining an inner surface and an outer surface opposite the inner surface, wherein the chemical substance is disposed adjacent to the inner surface;

positioning the liquid chemical substance adjacent to an opaque background material incorporated into the base portion with the opaque background material covering at least approximately the entire base portion, wherein the background material is positioned between the inner surface and the outer surface, between the outer surface and a protective coating, or between the inner surface and the chemical substance;

disposing a titrating agent in the vessel;

stirring the contents of the vessel; and detecting an equivalence point of the contents of the vessel by viewing the chemical substance through the wall portion while the chemical substance is positioned adjacent to the opaque background material and determining an amount of the titrating agent added to the vessel when the contents of the vessel changes from a first color to a second color different than the first color.

18. The method of claim 17 wherein the background material extends over a portion of the vessel wall, and wherein the method further comprises viewing the chemical substance against both the portion of the background material extending over the vessel base and the portion of the background material extending over the vessel wall.

* * * * *